(12) United States Patent
Chen et al.

(10) Patent No.: US 9,084,531 B2
(45) Date of Patent: Jul. 21, 2015

(54) PROVIDING REAL-TIME MARKER DETECTION FOR A STENT IN MEDICAL IMAGING

(71) Applicants: Terrence Chen, Princeton, NJ (US); Yu Wang, Centerville, OH (US); Peter Durlak, Erlangen (DE); Dorin Comaniciu, Princeton Junction, NJ (US)

(72) Inventors: Terrence Chen, Princeton, NJ (US); Yu Wang, Centerville, OH (US); Peter Durlak, Erlangen (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 83 days.

(21) Appl. No.: 13/778,454

(22) Filed: Feb. 27, 2013

(65) Prior Publication Data

US 2014/0241599 A1    Aug. 28, 2014

(51) Int. Cl.
G06K 9/00    (2006.01)
A61B 5/00    (2006.01)
A61B 6/12    (2006.01)
G06T 7/00    (2006.01)
A61B 6/00    (2006.01)

(52) U.S. Cl.
CPC .................. *A61B 5/0033* (2013.01); *A61B 6/12* (2013.01); *A61B 6/487* (2013.01); *A61B 6/5217* (2013.01); *A61B 2576/02* (2013.01); *G06T 7/0012* (2013.01)

(58) Field of Classification Search
CPC ........... A61B 6/12; A61B 6/503; A61B 6/504
USPC ....................................................... 382/128
See application file for complete search history.

(56) References Cited

U.S. PATENT DOCUMENTS

2011/0144480 A1* 6/2011 Lu et al. ...................... 600/424

* cited by examiner

*Primary Examiner* — Tom Y Lu

(57) ABSTRACT

Real-time marker detection in medical imaging of a stent may be provided. A plurality of frames of image data may be obtained. A plurality of candidate markers for the stent may be determined in the plurality of frames of image data. One or more markers from the plurality of candidate markers may be detected. The detecting may be based on automatic initialization using a subset of frames of image data from the plurality of frames of image data. The detecting may be performed in real-time with the obtaining.

20 Claims, 3 Drawing Sheets

PROVIDING REAL-TIME MARKER DETECTION FOR A STENT IN MEDICAL IMAGING

RELATED APPLICATIONS

The present patent application claims the benefit of the filing date under 35 U.S.C. §119(e) of U.S. Provisional Patent Application Ser. No. 61/603,514, filed Feb. 27, 2012, which is hereby incorporated by reference herein in its entirety.

BACKGROUND

The present embodiments relate to real-time marker detection in medical imaging.

Coronary heart disease, which is a narrowing of the coronary arteries, is the leading cause of death for both men and women. To treat coronary heart disease, an intervention, such as a Percutaneous Coronary Intervention (PCI) procedure, may be used. During the PCI procedure, a balloon-equipped stent is inserted into the coronary artery. A guide wire body inside the balloon is anchored by markers that provide visual indication of the position of the balloon and the stent. Once the stent reaches the desired position, the balloon expands the stent, which is, in turn, permanently left in the coronary artery.

Proper visualization of the stent, including the location of the stent, the surrounding tissue, and geometry of the stent is important to ensure the quality of the stent deployment and stent expansion. Stent under-expansion may lead to stent thrombosis and restenosis. Stent deployment is typically monitored by X-ray fluoroscopy, in which the visibility of the guide wire, markers, and the stent is often quite low. Due to poor visibility, poor contrast, nearby similar structures, and the rapid motion of the markers (due to, for example, cardiac and breathing motion), physicians often have a difficult time precisely deploying and/or expanding the stent using real-time fluoroscopic images. Accordingly, the stent may not be implanted precisely at the desired location and/or the stent may not be properly expanded against the artery wall.

Various image processing techniques have been proposed to improve the quality of fluoroscopy images and, in turn, provide better stent visibility. One example is motion-compensated noise reduction applied via a landmark-based registration of multiple images. Another example is a low-level image processing technique known as blob detection. Such image processing techniques may, however, produce many false positives, are conducted offline such that the physician can only observe the stent in one static image, result in information being lost and/or distorted, or require significant user intervention (e.g., for initialization, correction, and/or selection).

BRIEF SUMMARY

In order to provide better visual assistance to physicians during stent implementation and/or deployment, a robust tracking framework that provides real-time marker detection in medical imaging may be provided.

In a first aspect, a method of providing real-time marker detection in medical imaging of a stent is provided. A plurality of frames of image data is obtained. A plurality of candidate markers is determined for the stent in the plurality of frames of image data. One or more first markers from the plurality of candidate markers are detected. The detecting is based on automatic initialization using a subset of frames of image data from the plurality of frames of image data. The detecting is performed in real-time with the obtaining.

In a second aspect, a non-transitory computer-readable storage medium has stored therein data representing instructions executable by a programmed processor for providing real-time marker detection in medical imaging for a stent. The instructions include obtaining a plurality of frames of image data, determining a plurality of candidate marker pairs for the stent in the plurality of frames of image data, and tracking one or more marker pairs from the plurality of candidate marker pairs for the stent, the tracking being automatically initialized using a subset of frames of image data from the plurality of frames of image data, and the tracking performed in real-time with the obtaining.

In a third aspect, a system for providing marker detection in medical imaging is provided. The system includes a memory configured to store fluoroscopic image data. The system includes a processor configured to determine a plurality of candidate marker pairs and to automatically initialize a detector for tracking one or more candidate marker pairs of the plurality of candidate marker pairs. The detector is automatically initialized using a subset of the fluoroscopic image data. The processor is configured to track, in real-time, the one or more candidate marker pairs for a stent in the fluoroscopic image data using the automatically initialized detector. The processor is configured to generate an image of the stent based on the tracking. The system further includes a display configured to display the image of the stent.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the FIGS. are not necessarily to scale, emphasis instead being placed upon illustrating the principles of the invention. Moreover, in the FIGS., like reference numerals designate corresponding parts throughout the different views.

DETAILED DESCRIPTION OF THE DRAWINGS AND PRESENTLY PREFERRED EMBODIMENTS

The present embodiments aim to more effectively detect stent markers in medical imaging. To this end, one or more of the present embodiments provides a robust, self-initializing, and marker detection framework that may reduce the occurrences of false positives, provide real-time stent-associated guidance to the physician throughout the medical intervention, and/or not require significant user intervention (e.g., it automatically initializes). Advantageously, one or more of the present embodiments may also provide a higher-quality stent enhancement and, better yet, an enhancement that allows the physician to clearly visualize the stent in its original context. In other words, no information is lost or distorted in the scene.

One or more of the present embodiments rely on balloon markers to enable real-time enhanced visualization and assessment of the stent positioning and expansion, together with the blood flow over a lesion area. In one or more of the present embodiments, an automatic tracking framework is used that includes a self-initialization phase based on the Viterbi algorithm and an online tracking phase implementing the Bayesian fusion of multiple cues. The resulting motion compensation stabilizes the image of the stent and, by compounding multiple frames, a better stent contrast is obtained.

Figure 1:
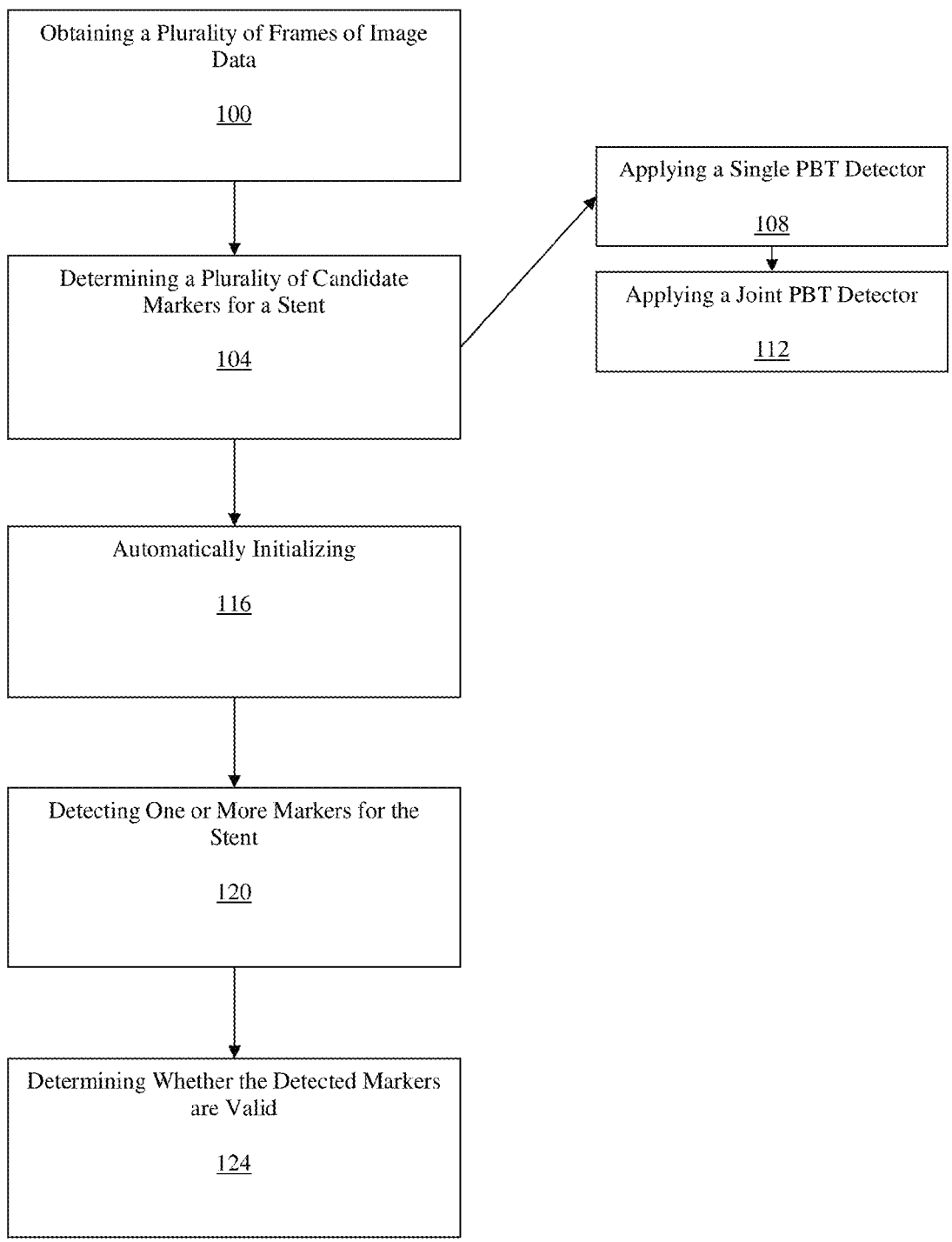
FIG. 1 is a flow chart diagram of one embodiment of a method for marker detection for a stent in medical imaging.

FIG. 1 shows a flow chart depicting a method for real-time marker detection for a stent in medical imaging. The method may be implemented using or by a medical diagnostic imaging system (e.g., a fluoroscopy system), a review station, a workstation, a computer, a picture archiving and communications system (PACS) station, a server, combinations thereof, or other device for image processing medical data. For example, the system or computer readable media shown in FIG. 3 may implement the method, but other systems may be used.

The method depicted in FIG. 1 generally includes obtaining a plurality of frames of image data (act 100), determining a plurality of candidate markers for a stent (act 104), automatically initializing (act 116), detecting one or more markers for the stent from the plurality of candidate markers (act 120), and determining whether the one or more detected markers are valid (act 124). Additional, different, or fewer acts may be provided. For example, act 116 and/or act 124 need not be provided. The method is implemented in the order shown, but may be implemented in or according to any number of different orders. Some of the acts, such as act 124, may be performed in real-time, such as during scanning of the patient, while the patient is undergoing stent placement, and/or during a medical intervention (e.g., a medical procedure such as PCI). The user may, for example, detect or track one or more markers while scanning to acquire additional frames of image data. Alternatively, the frames of image data are associated with previously acquired scanning or are provided after scanning Not all of the frames of the sequence may be available at the time of processing.

In act 100, a plurality of frames of image data may be obtained (e.g., acquired, scanned, loaded, or received). The frames of image data may include or correspond to image data obtained using any number of medical imaging devices. In one embodiment, the frames of image data are frames of fluoroscopy image data obtained during x-ray fluoroscopy. In other embodiments, the frames of image data may be or include frames of x-ray, computed tomography, ultrasound, magnetic resonance, or other types of imaging data.

Any number of frames of image data may be obtained. For example, 2, 10, 50, or 100 frames of image data may be obtained. The frames of image data may, in some embodiments, be obtained as part of an input sequence or stream of frames of image data. For example, a sequence (e.g., a live video fluoroscopy stream) of frames of fluoroscopy image data may be obtained. The input sequence may include any number of frames of image data, such as, for example 30-50 frames of fluoroscopic image data.

Each frame of image data represents a region of interest of a patient at a different time, such as, for example, during a medical intervention (e.g., PCI). The region of interest includes a stent, a balloon for expanding the stent, a guide wire, and one or more markers associated with (e.g., for, on) the stent. The one or more markers, which are radiopaque in order to be viewable in images, are indicative of a position of the stent. In one embodiment, the one or more markers are or include one or more balloon markers, such as a pair of balloon markers (e.g., a pair on each end of the balloon or near ends of the stent). Alternatively, or additionally, the guide wire and/or other structure associated with the stent may have or include one or more markers. Other markers may be other parts of the stent, such as wires of the stent itself. By detecting the one or more markers associated with the stent, such as the one or more markers on the balloon, the position of the stent may be determined. In other embodiments, medical devices other than a stent may be used and one or more markers associated with those devices may be detected.

The region of interest may or may not include a contrast agent, or may include a contrast agent only at certain points in time (e.g., during certain phases of the medical intervention). Accordingly, none, some, or all of the frames of image data may include data representing contrast agent. In some embodiments, a sequence of frames of image data may include some frames of image data that include data representing contrast agent and some frames of image data that do not include or are substantially free from data representing contrast agent. For example, the sequence of frames may include frames of image data obtained as part of a fluoroscopy sequence (i.e., a sequence of frames of fluoroscopy image data) that begins with a contrast-free phase in which the contrast agent is not injected to completely fill and enhance the artery, proceeds with a contrast-filled phase in which the contrast agent is injected and the artery(ies) become(s) visible, and ends with a contrast-free phrase when the contrast and, in turn, the artery(ies) is (are) not visible. As used herein, being substantially free of such information may include some return by contrast agent, but not a sufficient amount to distinguish noise, tissue, or fluid.

In act 104, a plurality of candidate or possible markers for a stent is determined (e.g., detected). Any number of candidate markers may be determined for the stent. For example, all candidate markers that satisfy the detection criteria may be detected. Alternatively, only a limited number of candidate markers may be detected, such as, for example, only those candidate markers detected before a detection limit is reached. The candidate markers may be or include candidate marker pairs. For example, the plurality of candidate markers may include five pairs of candidate marker pairs. The plurality of candidate markers for the stent may include only the one or more actual markers, may include the one or more actual markers and one or more other markers (e.g., locations in one or more frames of data that have similar characteristics), or may include only one or more other markers (i.e., not the actual markers).

The plurality of candidate markers for the stent is determined by applying one or more marker detectors to at least some of the plurality of frames of image data obtained in act 100. In some embodiments, only one marker detector is applied to at least some of the plurality of frames of image data. In one embodiment, one marker detector is applied to each of the plurality of frames of image data. In other embodiments, two or more marker detectors are applied to at least some of the plurality of frames of image data. One or more of these marker detectors may be applied to the same or different frames of image data. In one embodiment, two or more marker detectors are applied to each frame of image data in the plurality of frames of image data. For example, two marker detectors may be applied to each frame of fluoroscopy image data in the fluoroscopy sequence. In some embodiments, two or more marker detectors may be applied in a serial or hierarchical manner. For example, one marker detector may be applied to determine the plurality of candidate markers, and another marker detector may be applied to determine candidate marker pairs from the determined plurality of candidate markers.

The one or more marker detectors may be or include individual or single marker detectors, joint marker detectors, or combinations thereof. Each marker detector may be a marker detector trained offline as a classifier. One or more of the marker detectors may be trained using the same technique. For example, two marker detectors may be trained using the same technique. Alternatively, all of the marker detectors may be trained using different techniques. The resulting classifier may be or include a probabilistic boosting tree (PBT) classifier (e.g., a tree-based structure with which the posterior probabilities of the actual presence of the candidate marker is calculated), a cascaded classifier, a hierarchal classifier, multi-class classifier, model-based classifier, a machine learning-based classifier, or combinations thereof. Exemplary multi-class classifiers include CART, K-nearest neighbors, neutral network (e.g., multi-layer perceptron), mixture models, or the like. The classifier may be trained using features, such as, for example, Haar wavelet features, Haar wavelet-like features, steerable features, or other features. Any number of features may be used (e.g., tens, hundreds, or thousands of features). The classifier may be trained in any known manner. For example, one classifier may be trained using manually annotated samples collected from frames of image data in both contrast-free and contrast-filled phases. Alternatively, or additionally, one or more of the marker detectors may be trained using or based on the detection results (e.g., the plurality of candidate markers) provided by another marker detector.

In one exemplary embodiment, two marker detectors are applied in a hierarchical manner. In this exemplary embodiment, a single PBT detector is applied (act 108) to each of the plurality of frames of image data obtained in act 100. Subsequently, a joint PBT detector, trained with the candidate markers against false alarms (e.g., false positives) obtained from the application of the single PBT detector, is applied to the output from act 108 (act 112). In turn, the joint PBT detector outputs a set of candidate markers and a confidence value for each of the candidate markers.

The one or more marker detectors applied to at least some of the plurality of frames of image data may individually or jointly provide (e.g., output) the detected candidate markers. A score or probability may be provided for each candidate marker or marker group. The score or probability generally indicates the likelihood (e.g., probability, confidence, etc.) that the respective candidate marker is an actual marker. The score may be a binary score, some other score with a greater dynamic range, or a confidence score or value. When the score is a confidence score, the score is indicative of the marker detector's (or the marker detectors') confidence that the respective candidate marker is an actual marker. The confidence score is, in one embodiment, represented by $P(I_t|c_{t,m})$, where $c_{t,m}$ represents the mth candidate marker, and $I_t$ is the image. Higher scores may be indicative of a greater likelihood that the respective candidate marker is an actual marker. Alternatively, higher scores may be indicative of a lower likelihood that the respective candidate marker is an actual marker. When each candidate marker is provided with an associated probability, the probability generally indicates the probability that the candidate marker is actually present (i.e., that the candidate marker is an actual marker).

Despite applying one or more marker detectors, and applying two PBT marker detectors in the exemplary embodiment, some or all of the plurality of candidate markers may still be or represent false positives (i.e., they are not actual markers), particularly for frames of image data from or corresponding to the contrast-filled phase. As a result, the candidate marker or candidate marker pair with the highest (or lowest) score, highest (or lowest) confidence, and/or highest (or lowest) probability may not be the target (actual) marker or marker pair.

To address these problems, robust, real-time tracking is applied or utilized. In some embodiments, the real-time tracking includes or involves an automatic initialization (act 116) and real-time detection of one or more markers for the stent from the plurality of marker candidates based, at least in part, on the automatic initialization (act 120). In other embodiments, the tracking framework may include additional, different, or fewer acts. For example, the tracking framework may also include determining whether one or more of the detected markers are valid (e.g., is an actual marker) (act 124).

In act 116, the tracking is automatically initialized. The tracking is automatically initialized using or with a subset of frames of image data from the plurality of frames of image data. Stated another way, a detector is automatically initialized using or with the subset of frames of image data. The subset of frames may include some or all of the plurality of frames of image data. In one embodiment, the subset of frames includes a specified number of the first frames of image data in the sequence. For example, the subset of frames may include the first 10 frames of fluoroscopy image data from the live fluoroscopy stream.

Given the output (e.g., the plurality of candidate markers, the plurality of candidate marker pairs) provided by the one or more marker detectors, the automatic initialization involves determining (e.g., finding, detecting) one or more optimal candidate markers from the output for the subset of frames of data. More specifically, the automatic initialization may involve determining one or more optimal candidate markers from the output for each frame of data (i.e., at each time t, t+1, etc.) in the subset of frames of data. For example, the automatic initialization may involve finding an optimal candidate marker pair for each frame of data in the subset. Alternatively, the automatic initialization may involve determining one or more optimal candidate markers from the output for some, but not all, of the frames of data in the subset.

In one embodiment, the determining may be done by identifying the one or more optimal candidate marker pairs from the output that maximizes the posterior probability given by:

$$\hat{X} = \underset{X}{\operatorname{argmax}} P(X \mid Y), \quad (1)$$

where $X=\{x_1, \ldots, x_T=10\}$ is the state sequence, and $x_{t,k}=(b_{t,k},e_{t,k})$ is the kth state of the marker pair $b_{t,k}$ and $e_{t,k}$ at time t. $Y=\{I_1, \ldots, I_{T=10}\}$ are the images. In other embodiments, one or more optimal candidate markers may be determined in this way, or the determining may be done in a different way. For example, other cost functions may be used.

The one or more optimal candidate markers that maximize the posterior probability given by equation (1) are identified by applying or utilizing an algorithm. In one embodiment, the algorithm is a Viterbi algorithm, which may be used to find the most likely sequence of hidden states (known as the "Viterbi path"), but, in other embodiments, other algorithms may be applied or used.

One or more marker pair candidates that maximize the posterior probability given by equation (1) are identified by applying the Viterbi algorithm. The Viterbi algorithm may recursively find the weight of the most likely state sequence ending with each $x_{t,k}$ ($V_{t,k}$) at time t:

$$V_{1,k} = P(I_1 \mid x_{1,k})P(x_1, k); \qquad (2)$$

$$V_{t,k} = P(I_t \mid x_{t,k}) \max_j (P(x_{t,k} \mid x_{t-1,j})V_{t-1,j}), \qquad (3)$$

where $P(x_{1,k})$ the prior probability of the kth marker at or in a first frame of the subset of frames and is set to 1. $P(I_t|x_{t,k})$ represents the observation probability, which may be defined as the sum of the detection confidences of both candidate markers output by the one or more marker detectors:

$$P(I_t|x_{t,k}) \propto P(I_t|b_{t,k}) + P(I_t|e_{t,k}) \qquad (4)$$

where $P(x_{t,k}|x_{t-1,j})$ represents the transition probability from the jth state of time t−1 to the kth state of time t and is defined as a combination of the length consistency (i.e., the length between the two candidate markers), the direction consistency (e.g., direction change), and the movement or motion probability:

$$P(x_{t,k}|x_{t-1,j}) \propto U_{motion} * U_{length} * U_{dir}, \qquad (5)$$

where $U_{motion} = \exp(-(\|b_{t,k} - b_{t-1,j}\| + \|e_{t,k} - e_{t-1,j}\|)/\sigma)$, $U_{length} = \exp(-|l_{t,k} - l_{t-1,j}|/l_{t-1,j})$, and $U_{dir} = \max((b_{t,k} - e_{t,k}) \cdot (b_{t-1,j} - e_{t-1,j})/(l_{t,k} \cdot l_{t-1,j}), 0)$, with $l_{t,k} = \|b_{t,k} - e_{t,k}\|$ and $l_{t-1,j} = \|b_{t-1,j} - e_{t-1,j}\|$, σ may set to any value. For example, σ may be set to 100.

Figure 2:
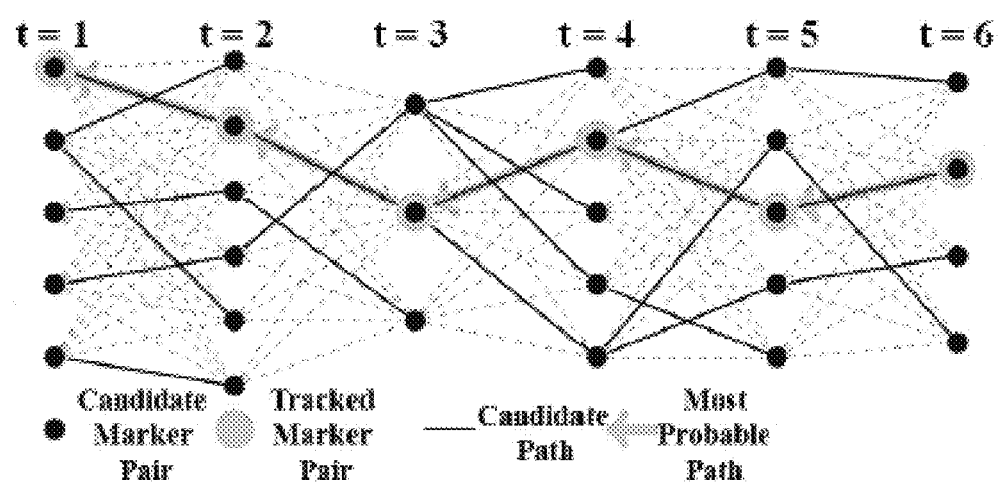
FIG. 2 shows an exemplary most probable path determined using a Viterbi algorithm.

In turn, the Viterbi algorithm may find the most probable path including the one or more optimal candidate marker pairs. FIG. 2 illustrates an exemplary most probable path determined using the Viterbi algorithm. The best or optimal state (i.e., the best or optimal marker(s)) in time T is found using $x_T = \arg\max_k(V_{T,k})$. The best or optimal states in or at other times may be found by backtracking the Viterbi path. In some embodiments, a heuristic may be applied to the most probable or best path to invalidate (e.g., remove) frames of image data with inconsistent motion or inconsistent marker pair distance.

The automatic initialization may, in some embodiments, also include generating a template T of or for the one or more optimal candidate markers. In one embodiment, the automatic initialization includes generating a joint template T of or for the one or more optimal candidate marker pairs. In some embodiments, the template is generated at or near the end of the automatic initialization act, but, in other embodiments, the template may be generated at a different time.

The automatic initialization may, in some embodiments, further include generating one or more Gaussian models to model the characteristics of the one or more optimal candidate markers (e.g., one or more optimal candidate marker pairs). In one embodiment, four Gaussian models ($l \sim N(u_{length}, \sigma_{length})$, $w \sim N(u_{width}, \sigma_{width})$, $h \sim N(u_{height}, \sigma_{height})$, $m \sim N(u_{motion}, \sigma_{motion})$) are generated to model the lengths, widths, heights (e.g., the bounding box of the respective candidate marker pair), and movements, respectively, of the one or more candidate marker pairs. The widths and heights may define the shape, such that these models may model the shape constinency. In other embodiments, a different number of models may be generated, different models (e.g., non-Gaussian models) may be used, different characteristics may be modeled, or combinations thereof.

In act 120, the tracking includes detecting one or more markers for the stent from the output (e.g., the plurality of candidate marker pairs) of act 104. The tracking is performed online or, in other words, in real-time. In other embodiments, some of the tracking (e.g., the detecting) may be performed at different times (e.g., not in real-time).

The tracking in act 120 aims to compensate for, or at least minimize the effect of, the above-noted errors (e.g., false positives) associated with only applying the one or more marker detectors and, in turn, more effectively detect or find the one or more actual markers for the stent. The tracking in act 120 may compensate for these errors by detecting based, at least in part, on the automatic initialization. The tracking in act 120 may, for example, utilize and/or update data (e.g., the one or more candidate markers), the template, one or more statistical models (e.g., the generated Gaussian models), or combinations thereof, obtained (e.g., generated) during the automatic initialization. Based on the data, template, models, or combinations thereof, the tracking in act 120 may adjust the scores or probabilities (e.g., the confidence scores) associated with each candidate marker provided by the one or more marker detectors.

The template T, which may be generated as part of the automatic initialization, may be updated or adapted during the tracking in act 120. In one embodiment, this is done using the following equation:

$$T = (1-\lambda)T + \lambda T_t, \qquad (6)$$

where λ is the learning rate. In one embodiment, the learning rate is set to 0.1. In other embodiments, the learning rate may be set to a different number. In other embodiments, the template T may be different or may be adapted in a different way.

The one or more Gaussian models, which may be generated as part of the automatic initialization, may be updated or adapted during the tracking in act 120. In the embodiment described above in which four Gaussian models ($l \sim N(u_{length}, \sigma_{length})$, $w \sim N(u_{width}, \sigma_{width})$, $h \sim N(u_{height}, \sigma_{height})$, $m \sim N(u_{motion}, \sigma_{motion})$) are generated to model the lengths, widths, heights, and movements of the marker pair, the models may updated during the tracking in act 120. The Gaussian model generated to model the length of the marker pair may, for example, be updated with the length of the tracked marker pair as follows:

$$u_{length}^t = (1-\lambda)u_{length}^{t-1} + \lambda \hat{l}_t \qquad (7)$$

$$(\sigma_{length}^t)^2 = (1-\lambda)(\sigma_{length}^{t-1})^2 + \lambda(\hat{l}_t - u_{length}^t)^2 \qquad (8),$$

where, as noted above, λ is the learning rate. In one embodiment, the learning rate is set to 0.1. In other embodiments, the learning rate may be set to a different number. The other Gaussian models, the Gaussian models generated to model the widths, heights, and movements of the marker pair, respectively, may be updated in a similar way. In other embodiments, one or more other models may be updated in a similar manner and/or one or more of the Gaussian or other models may be updated in a different manner.

Each of the one or more marker candidates provided by the one or more marker detectors may be evaluated. In one embodiment, each of the marker pair candidates provided by the single PBT detector or the joint PBT detector is evaluated. In this embodiment, the marker pair candidates are evaluated with or by a score $U(x_{t,k})$. The score $U(x_{t,k})$ is, in this embodiment, defined as or given by:

$$U(x_{t,k}) = P(I_t|x_{t,k}) * U_{tmp} * U_{motion} * U_{dir} * U_{shape}, \qquad (9)$$

where $P(I_t|x_{t,k})$ is the average of the detection confidences of the two marker candidates of the pair in $x_{t,k}$, $U_{tmp}$ is the product of the matching score between the template generated with the marker pair $x_{t,k}$ and the adaptive or updated joint template and the matching score between the template of $x_{t,k}$ and the template of the tracking result $\hat{x}_{t-1}$ at time t−1, $U_{motion} = \exp(-|d(x_{t,k}, \hat{x}_{t-1}) - u_{motion}|/\sigma_{motion})$ with $d(x_{t,k}, \hat{x}_{t-1})$ being the average movement of the marker candidates of the pair at time t from the tracked markers at time t−1, $U_{dir}$ is the dot product between the unit vector from $b_{t,k}$ to $e_{t,k}$ and the unit vector from $\hat{b}_{t-1}$ to $\hat{e}_{t-1}$, and $U_{shape}$ is the shape consistency. The shape consistency may be defined as follows:

$$U_{shape} = \exp\left(-\frac{|l_{t,k} - u_{length}|}{\sigma_{length}}\right) * \exp\left(-\frac{|h_{t,k} - u_{height}|}{\sigma_{height}}\right) * \exp\left(-\frac{|w_{t,k} - u_{width}|}{\sigma_{width}}\right), \quad (10)$$

where the terms are the length, height, and width probabilities, respectively. The one or more marker candidates provided by the one or more marker detectors may be evaluated in a similar or different way. For example, the one or more marker candidates may be evaluated using a different equation or the terms in the above-described equation may vary.

The scores for the candidate marker pairs may be evaluated (e.g., sorted, analyzed). For example, the candidate marker pairs may be sorted from highest score to lowest score. As another example, candidate marker pairs may be sorted from lowest score to highest score.

In some embodiments, based on the scores, one of the candidate marker pairs may be kept for each time t. The candidate marker pair kept for each time t may be selected as the final tracking result for that time. Alternatively, the candidate marker pair may be validated or verified as described in act 124 below. In other embodiments, based on the scores, two or more of the candidate marker pairs are retained or kept for each time t. Any number of candidate marker pairs may be kept for each time. In one embodiment, the five candidate marker pairs with the highest (or lowest) scores are kept. In another embodiment, the three candidate marker pairs with the highest (or lowest) scores are kept. The retained candidate marker pairs may be validated or verified as described in act 124.

In act 124, the one or more retained candidate marker pairs are validated or verified. Put another way, in act 124, it is determined whether the one or more retained candidate marker pairs are valid (i.e., are actual marker pairs). The validation is generally frame-specific. The validation may be performed for each frame of image data in the plurality of frames of image data or, alternatively, only for a portion thereof.

The one or more candidate marker pairs may be validated in any order. In some embodiments, the one or more candidate marker pairs may be validated in an order based on the scores from act 120. For example, the one or more candidate marker pairs are validated in order from highest scoring candidate marker pair to lowest scoring candidate marker pair. The highest scoring candidate marker pair is validated first. In another embodiment, the one or more candidate marker pairs are validated in order from the lowest scoring candidate marker pair to the highest scoring candidate marker pair. As will be described below, one or more of the candidate marker pairs need not be detected when one of the candidate marker pairs, such as the highest scoring candidate marker pair, is validated.

The validation of the detected candidate marker pairs is generally based on the adaptive Gaussian models and the adaptive template T equation utilized in act 120. More specifically, the validating is based on the adaptive Gaussian models generated to model the lengths and movements of the candidate marker pairs, the matching score between the adaptive joint template and the current template, and the matching score between the previous template and the current template.

In other embodiments, the validating may be based on additional, different, or fewer scores and/or models.

Based on the adaptive Gaussian models or the matching scores, one or more detected candidate marker pairs may be determined to be invalid or abnormal. One or more detected candidate marker pairs may be determined to be invalid when, for example, the length is abnormal (e.g., less than $u_{length}+\sigma_{length}$ or larger than $u_{length}-\sigma_{length}$), and/or the motion is too large (e.g., larger than $u_{motion}+\sigma_{motion}$). Alternatively or additionally, one or more detected candidate marker pairs may be determined to be invalid when, for example, one of the matching scores is too small (e.g., less than $u_{tmp}^{joint}-\sigma_{tmp}^{joint}$ or $u_{tmp}^{prev}-\sigma_{tmp}^{prev}$. In situations in which tracking is not successful in the frame of image data previous to or before the frame of image data corresponding to the one or more candidate markers currently being validated, the matching scores may not be considered. One or more detected candidate marker pairs may be determined to be invalid for other reasons as well.

When the respective candidate marker pair is determined to be invalid, the candidate marker pair is removed or discarded, and the next candidate marker pair (e.g., the next highest scoring candidate marker pair) is validated. The process continues (i.e., candidate marker pairs are validated) until one of the candidate marker pairs is determined to be valid (i.e., not invalid).

When one of the candidate marker pairs is determined to be valid, the respective candidate marker pair is selected as the final tracking result. In some embodiments, the parameters of the Gaussian models, the matching scores, the template T, or combinations thereof, may then be updated using the results (associated with the valid candidate marker pair) as described above. The influence of the invalid pairs is removed.

When, however, all of the retained candidate marker pairs are determined to be invalid, the tracking at that respective frame of image data may be labeled as failed or invalid. Any invalid frames may, in turn, be filtered out (e.g., removed), such that when the tracking results and the aligned frames of image data are generated and presented to the physician, the invalid frame(s) is (are) not reported. Instead, the empty frame(s), or no results, may be reported.

By validating the detected candidate marker pairs in this manner, the precision rate may be increased at the expense of a slightly lower recall rate (since the present embodiments will remove invalid frames of image data, but may also remove valid frames of image data in which the one or more actual markers are successfully tracked). Nevertheless, the present embodiments may improve the visual assistance provided during stent implementation and deployment by showing less tracking and alignment failures.

Using the one or more marker pairs in the valid frames of image data (e.g., each frame of image data), the stent information in different frames may be aligned. One or more aligned frames may be combined based on one or more criterion, such as, for example, frames corresponding to the same heart phase, frames of image data after the stent has been implanted, other criterion, etc. This results in the formation of an enhanced image of the stent. The enhanced image may be provided to a user (e.g., the physician). The enhanced image of the stent may provide visual assistance to the physician during stent implementation and/or deployment. A sequence of individual images from different frames may be generated with the detected markers highlighted.

In one embodiment, the method 100 described herein may be used to facilitate stent positioning during a medical procedure, such as PCI, where the main difficulty for physicians is to observe the balloon markers relative to the lesion and vessels. This may be quite challenging due to the rapid motion of coronary arteries during real-time monitoring. By stabilizing a scene using the location of the balloon markers, the medical procedure, such as PCI, may be improved. Accordingly, the balloon marker pair may be tracked in streaming data, the image may be transformed such that the balloon marker pair is always aligned at the same coordinates, and the transformed image may then be displayed to the physician. In one example, 10 images of frame data are used. In a typical 15 FPS acquisition rate, the self-initialization may take 0.67 seconds and the computation of the self-initialization may take 0.27 seconds, after which the real-time online detection may be utilized. Once the online detection starts, the new scene may be stabilized by the coordinates of the balloon marker pair. The physician may inject contrast and observe the relation between the marker pair (undeployed stent) and the lesion area. By self-initializing as described herein, the robustness of the tracking may be significantly improved. For example, applying a well-trained detector to a single image may result in a detection accuracy of about 82%, whereas applying the tracking described herein may yield a detection accuracy of about 97%, a 15% improvement in terms of the detection accuracy.

In another embodiment, the method 100 described herein may assist physicians in assessing the real-time stent expansion or deployment. Once the marker pairs are localized in or during the automatic initialization, a motion-compensated based stent enhancement may be applied to obtain a stent enhancement image (SEI). To ensure that the SEI is of a sufficient quality, the subset of frames of image data used during the automatic initialization may be set to 25 frames of image data. After the real-time tracking begins, a compound of the SEI and the streaming data may be output as the visual result to the physician. Specifically, the SEI may be obtained by $\{f_1, \ldots, f_{25}\}$, with $f_1 \ldots f_t$ being the t frames of image data of the input data stream. Once the SEI is obtained, a guidewire localization technique may be applied to the SEI to obtain the guidewire $\tau$ that passes through the two markers. A weighting field W may then be generated by applying a Gaussian kernel to the guidewire location on SEI. Once the real-time tracking begins, which may begin between frame of image data 40 and 45 ($f_{40}$ to $f_{45}$), the SEI may be rigidly transformed to $\hat{SEI}$ such that the marker pair of $\hat{SEI}$ is aligned with the marker pair in the current frame $f_i$. The output image $\hat{f}_i$ may then be obtained by compounding the $\hat{SEI}$ and $f_i$ with W:

$$\hat{f}_i = W \times \hat{SEI} + (1-W) \times f_i,$$

where i is the frame index, which normally begins with 40 to 45. In other words, the computation time for the SEI may be up to 3 seconds in a 15 FPS acquisition.

When, for example, a real-time or live acquisition is followed by a playback, the same enhancement may be applied to the frames during the automatic initialization and the computation thereof as well. In other words, during the playback mode, the stent may be enhanced in every frame.

Based on the clinical preference, scene stabilization based on the balloon markers, as described herein, may be provided during stent enhancement and/or assessment.

Figure 3:
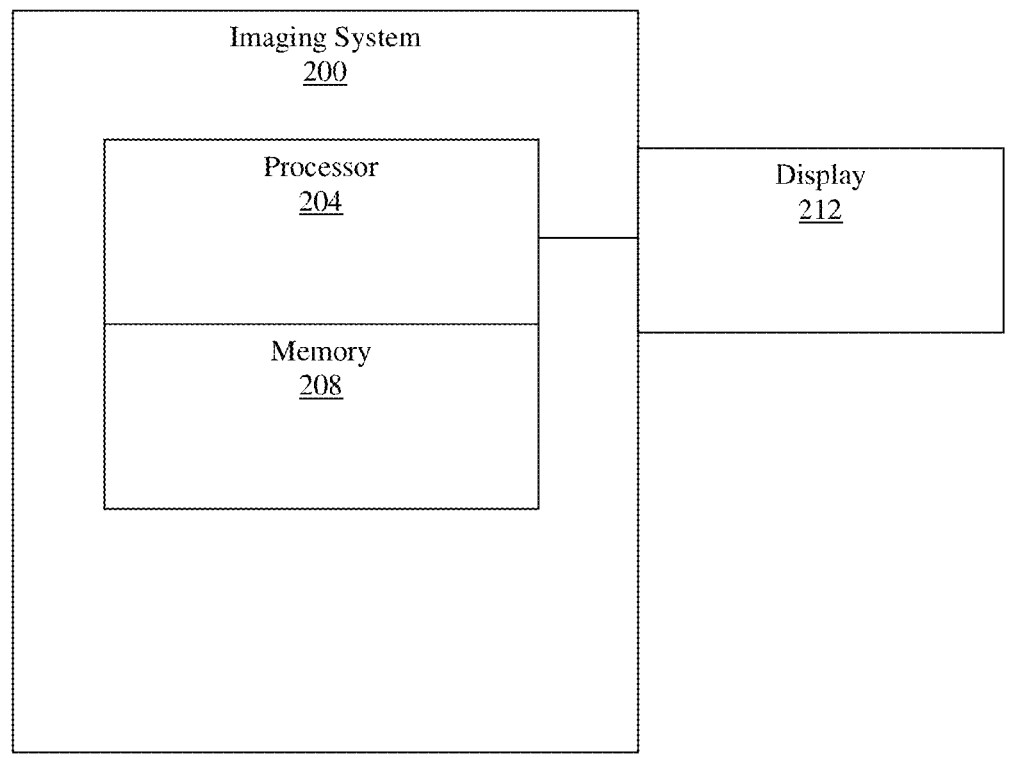
FIG. 3 is a block diagram of one embodiment of a system for marker detection for a stent in medical imaging.

FIG. 3 shows a medical diagnostic imaging system 200 for real-time marker detection in medical imaging. The system 200 is a medical fluoroscopy imaging system, but may be a computer, workstation, database, server, or other system. The system 200 includes a processor 204, a memory 208, and a display 212. In other embodiments, the system 200 may include additional, different, or fewer components. For example, the system 200 may include an x-ray source and detector.

The memory 208 is a buffer, cache, RAM, removable media, hard drive, magnetic, optical, database, or other now known or later developed memory. The memory 208 is a single device or group of two or more devices. The memory 208 is shown within the system 200, but may be outside or remote from other components of the system 200, such as a database or PACS memory.

The memory 208 stores medical imaging data, particularly frames of medical imaging data. Any type of medical imaging data (e.g., fluoroscopy, magnetic resonance, CT, etc., imaging data) may be stored. For example, a sequence of frames of fluoroscopy imaging data is stored. The sequence is acquired over seconds or minutes. The medical images are of a region including a vessel, a stent, and/or markers (e.g., a pair of markers on a balloon for the stent). The stent may be introduced during acquisition of the sequence or may already be in place during the acquisition. The vessel may or may not include a guide wire for placement of the stent. The data includes a representation of two or more markers for the stent. Alternatively, the medical image data is transferred to the processor 204 from another device with or without storage in the memory 208.

For real-time imaging, the medical data bypasses the memory 208, is temporarily stored in the memory 208, or is loaded from the memory 208. Real-time imaging may allow delay of a fraction of seconds, or even seconds, between acquisition of data and imaging. For example, real-time imaging is provided by generating images of the sequence substantially simultaneously with the acquisition of the data by scanning. To allow better visualization of the stent, especially stents with less metal or radio opaque materials, an enhanced stent image may be generated. In alternative embodiments, the image data is stored in the memory 208 from a previous imaging session and used for detecting markers and/or generating stent enhanced images.

The memory 208 is additionally or alternatively a non-transitory computer readable storage medium with processing instructions. The memory 208 stores data representing instructions executable by the programmed processor 204 for marker detection in medical imaging in medical imaging of a stent. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and non-volatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 204 is a general processor, digital signal processor, graphics processing unit, application specific integrated circuit, field programmable gate array, digital circuit, analog circuit, combinations thereof, or other now known or later developed device for processing frames of data for medical images. The processor 204 is a single device, a plurality of devices, or a network. For more than one device, parallel or sequential division of processing may be used. Different devices making up the processor 204 may perform different functions, such as a marker detector and a separate device for generating a stent enhanced image. In one embodiment, the processor 204 is a control processor or other processor of a medical diagnostic imaging system, such as a fluoroscopy imaging system processor. The processor 204 operates pursuant to stored instructions to perform various acts described herein, such as obtaining frames of image data, determining a plurality of candidate markers, automatically initializing a detector, tracking one or more markers, providing an image of the stent based on the tracking, or combinations thereof.

The processor 204 is configured to perform any or all of the above-described acts (e.g., the acts illustrated in FIG. 1). The processor 204 is configured to obtain a plurality of frames of image data. The processor 204 is configured to determine a plurality of candidate markers for the stent in the plurality of frames of image data. The processor 204 is configured to detect one or more candidate markers from the plurality of candidate markers. The processor 204 is configured to automatically initialize the detection using a subset of frames of the image data from the plurality of frames of image data. The processor 204 is configured to detect based, at least in part, on the automatic initialization. The processor 204 is configured to detect in real-time.

The display 212 is a CRT, LCD, plasma, projector, printer, or other output device for showing an image. The display 212 displays an image of two or more markers. A stent enhanced image with markers enhanced and/or highlighted may be displayed. An image of marker characteristics may be displayed, such as displaying a value representing the distance between markers. In other embodiments, the markers are not displayed, are displayed to indicate the location, or are merely displayed as part of an image without highlighting or enhancement.

In one exemplary embodiment, quantitative evaluation is conducted on a database of 356 sequences with a total of 17,234 frames collected from worldwide clinics. Most images have a size of 1024×1024. Some images have a smaller size of 776×776 or 720×720, for example. The quantitative evaluation is performed using a PBT detector and using the tracking framework described herein.

Both a single marker detector and joint marker PBT detector are used. The top 2 PBT detections in terms of detection confidence are used as the detection result at each frame. In the experiments using the tracking described herein, two online boosting detectors are initialized that track the markers independently. 50 base classifiers are used in each detector and Haar features are employed. At each frame, the online boosting detector is updated with the tracking result (20 by 20 window centering at the tracked marker) as the positive sample and randomly sampled windows in the neighboring region as the negative samples.

The ground truth markers on the 17,234 frames are created using a semi-automated annotation method. The error distance threshold is set to 1.5 mm so that a tracked marker is not correct if it is more than 1.5 mm away from the target marker. This value is reasonable considering the size of the image and the scale of the balloon marker. This quantitative evaluation also involved a study of the tracking accuracy as a function of this threshold value.

First, the tracking framework described herein is quantitatively compared with the PBT detector (D) and a previous approach. The first 10 frames of each of the 356 sequences are used for initialization. Two measures are used for this evaluation—success and recall. Success is defined by when all returned marker pairs are correct. Recall is defined by the number of marker pairs that are localized and returned. On a total of 356 sequences, the accuracy of the present embodiments is about 29 percent higher than the PBT detector used without the tracking described herein (and without initialization) and 1 percent higher than the previous approach, as shown in Table 1 below. The PBT detector failed on 71 sequences, while the tracking framework described herein only failed at 11 sequences. These 11 sequences are mainly caused by marker-like objects that are consistently detected at the first 10 frames and one or both markers that are not detected by the PBT.

TABLE 1

| Part A. | POS.Success | POS. Recall |
| --- | --- | --- |
| D | 0.68 (285/356) | 100% |
| Previous Approach | 0.96 (342/356) | 78.9% |
| Present Embodiments | 0.97 (345/356) | 88.9% |

To evaluate the accuracy in the online tracking phase, the remaining 13,674 frames of the 356 sequences are used. For fair comparison of the online tracking accuracy, the automatic initialization described herein was applied to three different detection methods the PBT detection method (D), the online boosting detection method, and the detection framework described herein. As shown in Table 2 below, the tracking framework described herein outperformed the other two tracking methods and reached 96.50% accuracy and an average of 29.04 FPS.

TABLE 2

| Part B. | Accuracy | Accuracy after validation | FPS |
| --- | --- | --- | --- |
| D | 81.93% (11203/13674) | N/A | 35.54 |
| Online Boosting | 53.00% (7247/13674) | N/A | 9.08 |
| Present Embodiments | 96.50% (13195/13674) | 98.50% (12651/12844) | 29.04 |

By applying the validation approach (act 124), the accuracy is boosted to 98.50%.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

We claim:

1. A method of providing real-time marker detection in medical imaging of a stent, the method comprising:
   obtaining a plurality of frames of image data;
   determining a plurality of candidate markers for the stent in the plurality of frames of image data; and
   detecting, by a processor, one or more first markers for the stent from the plurality of candidate markers, the detecting being based on automatic initialization using a subset of frames of image data from the plurality of frames of image data, wherein the automatic initialization comprises applying an algorithm to the subset of frames of image data and determining a path through the subset of frames of image data based on the applying, detecting performed in real-time with the obtaining.

2. The method of claim 1, wherein obtaining the plurality of frames of image data comprises obtaining a plurality of frames of fluoroscopic image data.

3. The method of claim 1, wherein detecting the plurality of candidate markers for the stent comprises detecting a plurality of candidate marker pairs for the stent.

4. The method of claim 1, wherein the algorithm comprises applying a Viterbi algorithm to the subset of frames of image data and finding one or more first markers from the plurality of candidate markers based on the applying.

5. The method of claim 1, wherein detecting comprises detecting the one or more first markers for the stent based, at least in part, on one or more models generated during the automatic initialization to model one or more of the plurality of candidate markers.

6. The method of claim 5, wherein the detecting comprises updating the one or more models generated during the automatic initialization, and detecting the one or more first markers based, at least in part, on the updating.

7. The method of claim 1, wherein determining the plurality of candidate markers comprises applying a machine learning-based detector to the plurality of frames of image data.

8. The method of claim 1, further comprising:
   determining whether the detected one or more first markers are valid markers; and selecting a final tracking marker based on the determining.

9. The method of claim 8, wherein the determining comprises determining that the detected one or more first markers are not valid for a frame of image data of the plurality of frames of image data, the method further comprising removing the respective frame of image data.

10. In a non-transitory computer-readable storage medium having stored therein data representing instructions executable by a programmed processor for providing real-time marker detection in medical imaging for a stent, the storage medium comprising instructions for:
   obtaining a plurality of frames of image data;
   determining a plurality of candidate marker pairs for the stent in the plurality of frames of image data; and
   tracking one or more marker pairs from the plurality of candidate marker pairs for the stent, the tracking being automatically initialized using a subset of frames of image data from the plurality of frames of image data, wherein the automatic initializing comprises applying an algorithm to the subset of frames of image data, and the tracking performed in real-time with the obtaining.

11. The computer-readable storage medium of claim 10, wherein obtaining the plurality of frames of image data comprises obtaining a plurality of frames of fluoroscopic image data.

12. The computer-readable storage medium of claim 10, wherein the automatic initializing comprises generating a plurality of Gaussian models to model one or more of the plurality of candidate marker pairs, and wherein the tracking of the one or more marker pairs is based, at least in part, on the plurality of Gaussian models.

13. The computer-readable storage medium of claim 10, wherein the automatic initializing comprises generating a joint template for each of the plurality of candidate marker pairs, and wherein the tracking of the one or more marker pairs is based, at least in part, on the joint templates.

14. The computer-readable storage medium of claim 10, further comprising validating the tracked marker pairs.

15. The computer-readable storage medium of claim 10, wherein applying the algorithm comprises applying a Viterbi algorithm to the subset of frames of image data.

16. A system for providing real-time marker detection in medical imaging, the system comprising:
   a memory configured to store fluoroscopic image data;
   a processor configured to determine a plurality of candidate marker pairs and to automatically initialize a detector for tracking one or more candidate marker pairs of the plurality of candidate marker pairs, the detector automatically initialized using a subset of the fluoroscopic image data, the processor configured to track, in real-time, the one or more candidate marker pairs for a stent in the fluoroscopic image data using the automatically initialized detector, wherein the detector comprises applying an algorithm to the subset of the fluoroscopic image data, and the processor configured to generate an image of the stent based on the tracking; and
   a display configured to display the image of the stent.

17. The system of claim 16, wherein the processor is configured to generate a plurality of Gaussian models associated with the plurality of candidate marker pairs and a joint template for each of the plurality of candidate marker pairs, and wherein the processor is configured to track the one or more candidate marker pairs for the stent based, at least in part, on the plurality of Gaussian models and the joint templates.

18. The system of claim 16, wherein the processor is configured to determine whether one or more of the detected candidate marker pairs are valid.

19. The system of claim 18, wherein the processor is configured to determine that one or more of the detected candidate marker pairs is not valid when a length of the respective candidate marker pair is abnormal or a motion of the candidate marker pair is too large.

20. The system of claim 18, wherein, when the respective candidate marker pair is determined to be a valid marker pair, the processor is configured to select the respective candidate marker pair as a final tracking marker pair.

* * * * *